United States Patent [19]

Bachelder et al.

[11] Patent Number: 4,802,366

[45] Date of Patent: Feb. 7, 1989

[54] APPARATUS AND PROCESS FOR IMPACT TESTING OF PLASTICS

[75] Inventors: Walter F. Bachelder, Ft. Falonga; Maurice Frankel, Farmingville; Peter Fiore, Mt. Sinai, all of N.Y.

[73] Assignee: Testing Machines Inc., Amityville, N.Y.

[21] Appl. No.: 199,026

[22] Filed: May 26, 1988

[51] Int. Cl.$^4$ .............................................. G01N 3/30
[52] U.S. Cl. ....................................... 73/799; 73/844; 73/845
[58] Field of Search ................... 73/11, 799, 844, 856, 73/845

[56] References Cited

U.S. PATENT DOCUMENTS

3,763,698  10/1973  Suzuki et al. ................... 73/856 X
4,606,230   8/1986  Scott et al. ..................... 73/856

Primary Examiner—Jerry W. Myracle
Attorney, Agent, or Firm—Anthony J. Casella; Gerald E. Hespos

[57] ABSTRACT

An impact testing apparatus and process are provided. The apparatus comprises a thickness verifier to measure the thickness of each specimen. The apparatus further comprises a notcher and a notch verifier which are operative to first cut notches in a test group of specimens and to subsequently verify the accuracy of the notches. The apparatus further comprises a robotic gripper to sequentially deliver specimens to a vise for impact testing. The impact tester of the apparatus is operative to automatically assess the impact on each specimen. Additionally, the impact tester comprises optical sensors to assess the type of break of each specimen subjected to the impact test. A control unit receives input data from the various components of the apparatus, analyzes the data and prepares test reports.

17 Claims, 6 Drawing Sheets

APPARATUS AND PROCESS FOR IMPACT TESTING OF PLASTICS

BACKGROUND OF THE INVENTION

The manufacture of plastics involves the precise blending of various chemicals under carefully controlled process conditions. Variations of these process steps can substantially affect the characteristics and performance of the plastic. As a result, samples from batches of plastic are routinely tested to assess the performance of the plastics from a particular batch.

One widely used and important test assesses the reaction of the plastic to specified impact forces. The plastics industry employs an impact test performed precisely in accordance with ASTM standard #256 Method A (Izod type). In particular, the test employs a rectangular plastic specimen having a length of 2.500 inches, a width of 0.500 inch and a predetermined thickness of 0.125 inch, 0.250 inch or 0.500 inch. A V-shaped notch is formed in one edge of the plastic at a location midway along the length of the specimen. The notch is cut to a specified depth of 0.100±0.002, such that the width of the specimen below the notch is 0.400 inch±0.002 inch. The specimen is then securely clamped in a vise such that the apex of the notch is precisely aligned with the top of the vise. The portion of the specimen extending above the top of the vise is then impacted by a specified weight gravitationally falling through a specified arc. The particular weight employed in these tests is selected in accordance with the anticipated characteristics of the plastics being tested. The impact of the weight on the specimen is measured in appropriate units (e.g. foot-pounds/inch), with the type of break being noted and recorded (e.g. no break, partial break, hinged break or complete break). The test results of both the break type and the corresponding impact are then analyzed to determine if the plastic performed to its specifications.

The above described impact test is often performed for each batch of plastic being made. ASTM standards recommend that the impact tests be performed on ten specimens, with average readings then being compared to specifications.

The prior art impact testing procedures are labor intensive, slow, costly and often yield inaccurate results. In particular, the first step in the prior art testing procedure is to manually check the dimensions of each specimen with micrometers. If the specimen falls outside the established dimensional tolerances, it is discarded. Acceptable specimens are then manually notched. The prior art notching apparatus is intended only to receive two specimens at a time, with the second of the two specimens being discarded in view of inaccuracies that are likely as the prior art notch apparatus completes its cut. Attempts to insert more than two specimens in the prior art notch apparatus results in an upward or downward bowing of the linear array of specimens, with corresponding inaccuracies in the dimensions of the notch. In this regard, it must be emphasized that inaccuracies in either the dimensions of the specimen or the dimensions of the notch significantly affect the response of the specimen to the impact, and thereby yield inaccurate test results. The prior art manual measurement of the specimen and manual notching make errors likely with correspondingly inaccurate test results.

After the specimen is notched by the prior art apparatus, each specimen is manually mounted into an appropriate vise for completion of the prior art impact test. The test technician visually observes the specimen during and immediately after the impact test and records the foot-pounds/inch reading of the prior art impact tester. In the typical prior art apparatus, these individual test readings are manually recorded for subsequent analysis. Recently, certain improvements in the recordings of impact test results have been made. In particular, an impact tester has been employed with control means which store and analyze the foot-pounds/inch data from a plurality of tests, thereby avoiding the need for manual recording and analysis. An example of such a recent prior art impact testing apparatus is the Monitor/Impact tester sold by Testing Machines Inc.

Despite the recent advances in plastic impact testing devices, the testing processes continue to be extremely labor intensive, slow, costly and subject to errors in the measurement, notching and visual observation portions of the tests. For example, it is estimated that the notching of the above identified specimens of 0.125 inch thickness takes approximately 7.5 seconds per specimen with the prior art notching machinery. The verification of the notch depth is estimated to take approximately ten seconds per sample, while the verification of the thickness and other dimensional measurements of the specimen is estimated to take approximately five seconds per specimen. The actual impact testing of each specimen is estimated to take approximately 22 seconds per specimen, while the recording of the results and the calculations of the foot-pounds/inch may take an additional 15 seconds per specimen. This recording and calculating step can be substantially eliminated with the recently developed Monitor/Impact tester of Testing Machines Inc. However, even these recently developed impact test devices do not improve the time or quality of the notching, notch verification and thickness measurement steps as identified above. In view of these estimated times, an average test run consisting of 50 specimens would take approximately 60 minutes of operator using the typical prior art equipment, and would take approximately 45 minutes of operator time using a system that automatically records test results such as the Monitor/Impact tester of Testing Machines Inc.

In view of the substantial times involved, many plastics companies have full-time staff dedicated to the preparation of specimens and actual testing. The characteristics of the prior art systems require the staff members to devote their full attention to the tasks of preparing specimens and running impact tests.

In view of the above, it is an object of the subject invention to provide an efficient impact testing apparatus and process.

It is a further object of the subject invention to provide an impact testing apparatus and process that substantially minimizes the labor costs associated with plastics impact testing.

Another object of the subject invention is to provide an impact testing apparatus that enables more accurate impact testing results.

A further object of the subject invention is to provide an impact testing apparatus that automatically assesses and identifies the type of break in the plastic specimen.

SUMMARY OF THE INVENTION

The subject invention is directed to an apparatus for automatically and accurately performing impact tests on plastic specimens, and recording the results of said tests. The apparatus may further be operative to perform the impact tests and record the results sequentially for a plurality of different plastic specimens. Additionally, the apparatus may be operative to perform impact tests on a plurality of plastic specimens, with said plurality comprising a plurality of discrete test groups, with the specimens in each test group being analyzed separately from the other groups to enable separate impact test reports on each group. The different test groups may represent different batches of a plastic or entirely different types of plastic.

The apparatus comprises a control unit which is operative to receive input data which may include: the number of test groups being run sequentially; the number of specimens in each respective test group; an identification of the plastic's type and batch for each group; ambient temperature and other atmospheric conditions; impact pendulum characteristics; and the identity of the machine operator. The control unit may further coordinate with other parts of the apparatus to receive input therefrom and to coordinate the testing activities as explained herein.

The apparatus may further comprise means for receiving a plurality of specimens. In particular, the apparatus may comprise at least one magazine for receiving a plurality of specimens, including a plurality of different test groups.

The apparatus may further comprise means for verifying the dimensions of each specimen prior to testing. The specimen dimensional verification may be carried out by transducers or other electromechanical means. The dimensional verification means may be operatively connected to the control means such that the precise dimensions of the individual specimens may be recorded by the control unit for use in subsequent calculations and for subsequent reporting steps. For example, the control unit may disregard tests on specimens outside established dimensional tolerances.

The apparatus may further comprise scanner means for identifying specimens. Thus, all or selected specimens may be provided with a bar code to identify the batch of plastics from which the specimen was drawn. For example, one specimen at the beginning or end of each test group may be provided with identifying means such as a bar code to identify the group. In this example, the apparatus may be provided with optical scanning means for reading the bar code that may be present on the specimens. The scanner means may also be operative to initiate each test and to terminate the entire test. The scanner means may be operatively connected to the control unit to enable accurate analysis and reporting of specimens in accordance with their test group. The use of the scanner means reduces the amount of data that must be manually input to the control means.

The apparatus may further comprise notching means for precisely cutting the notches into the specimens. The notching means may comprise means for securely gripping a plurality of specimens, such as all of the specimens in a selected test group. The notching means may then cut an appropriately dimensioned, configured and located notch in the specimens. Means for verifying the accuracy of the notches may further be provided. For example, the notch verification means may comprise a mechanical or electromechanical apparatus such as an appropriately dimensioned anvil operatively connected to a transducer to check the dimensions of each notch. Alternatively, electro-optical means may be provided for checking the dimensions of each notch.

The apparatus further comprises means for accurately placing each notched specimen in a vise at which the impact testing will occur. In particular, the apparatus may comprise robotic grippers which are operative to sequentially grip notched specimens and appropriately place individual specimens in a vise such that the notch is properly aligned to the top of the vise, in accordance with ASTM standards.

The apparatus further comprises a pendulously mounted hammer which is operative to swing into contact with the specimen. The hammer has a predetermined mass and foot-pound capacity selected in accordance with the specimens being tested. The hammer further comprises means for determining the impact of the hammer on the plastic specimens in foot-pounds/inch or other appropriate units of measurement. The actual hammer and the impact measuring means may be similar to those used in existing prior art devices such as the Monitor/Impact apparatus sold by Testing Machines Inc. However, the impact tester is operatively connected to the control unit such that the impact measurements for each test are appropriately recorded by the control unit and are analyzed as part of the impact test for each sequential specimen being tested and for each test group.

The impact tester further comprises means for identifying the type of break occurring in the plastic specimen. For example, electro-optical means may be provided to assess the movement and/or final position of the top half of each tested specimen to identify the type of break. In a preferred embodiment, as explained further below, a plurality of optical sensors may be disposed in or adjacent the vise, and on the side of the specimen opposite the side being struck by the hammer. The optical sensors may be operative to sense the presence of the top half of the specimen which may be in line with at least one optical sensor depending upon the type of break. The optical sensors may be disposed such that no reading will be recorded in situations where the specimen does not break. However, partial break of the specimen may position the top specimen half in a position to be sensed by one of the optical sensors. More complete breaks may be sensed by more than one of the sensors. The means for identifying the type of break may also be in communication with the control unit such that the type of break is recorded as part of the test results for each specimen.

The apparatus may further comprise means for removing the remains of a specimen on which a test has been performed. The specimen removal means may comprise appropriate robotic grippers which are operative to move at least the lower half of the specimen from the vise to permit subsequent tests to proceed. In this regard, the movements of the specimens into and out of the vise and the appropriate gripping and releasing by the vise may also be controlled by the control unit.

The apparatus may further comprise display means such as a display screen and/or a printer. The display means is operatively connected to the control unit such that a complete report of test results may be provided for each specimen and/or for each test group of specimens.

The entire apparatus is automatic except for the initial coding of any test data that is not performed by the scanner means and the initial loading of specimens to be tested. The apparatus is operative to sequentially run a plurality of test groups of varying sizes, with the number of test groups and the number of specimens in each group being entered either manually by the tester or automatically by bar codes or other indicia on at least selected specimens. It is anticipated that an average test run consisting of 50 samples would take approximately 6 minutes of operator time, thereby freeing the operator for other work and substantially reducing the total test time. The person/hours required for the subject apparatus can provide a ten-to-one savings over the typical prior art testing procedure and an approximately eight-to-one savings over the known automatic testers that automatically record and calculate test results, such as the Monitor/Impact apparatus of Testing Machines Inc.

DETAILED DESCRIPTION OF THE PREFERRED EMBODIMENT

The impact testing apparatus of the subject invention is identified generally by the numeral 10 in FIGS. 1, 2, 5 and 6. As shown schematically in FIG. 1, the apparatus 10 comprises a control unit 12 which coordinates the activities of the other components of the apparatus, and which receives and analyzes information from both the operator of the apparatus and from the other components. Typically, the operator of the apparatus may enter into the control unit 12: his or her own identity; the date and time; ambient atmospheric conditions, including temperature; and information pertaining to the test to be run, including the number of test groups to be run, the identity of each group and the number of specimens in each of the respective groups. However, as noted above, the control unit may comprise or be in communication with scanner means for automatically reading encoded input data. It is not necessary for the respective test groups to include equal numbers of specimens. Although the control unit 12 may specifically coordinate the activities of each other part of the apparatus 10, the control unit may merely receive test data from other parts of the apparatus for subsequent mathematical analysis and reporting. In this regard, in its simplest form, the control unit 12 may merely be a data processing unit which is operative to receive input data from a plurality of sources and perform mathematical analysis based on that input data. The communication between the control unit 12 and the remainder of apparatus 10 preferably enables the control unit 12 to produce a signal identifying the existence and location of any jam in apparatus 10. A reset button to continue a test after clearing a jam may also be provided.

Figure 1:
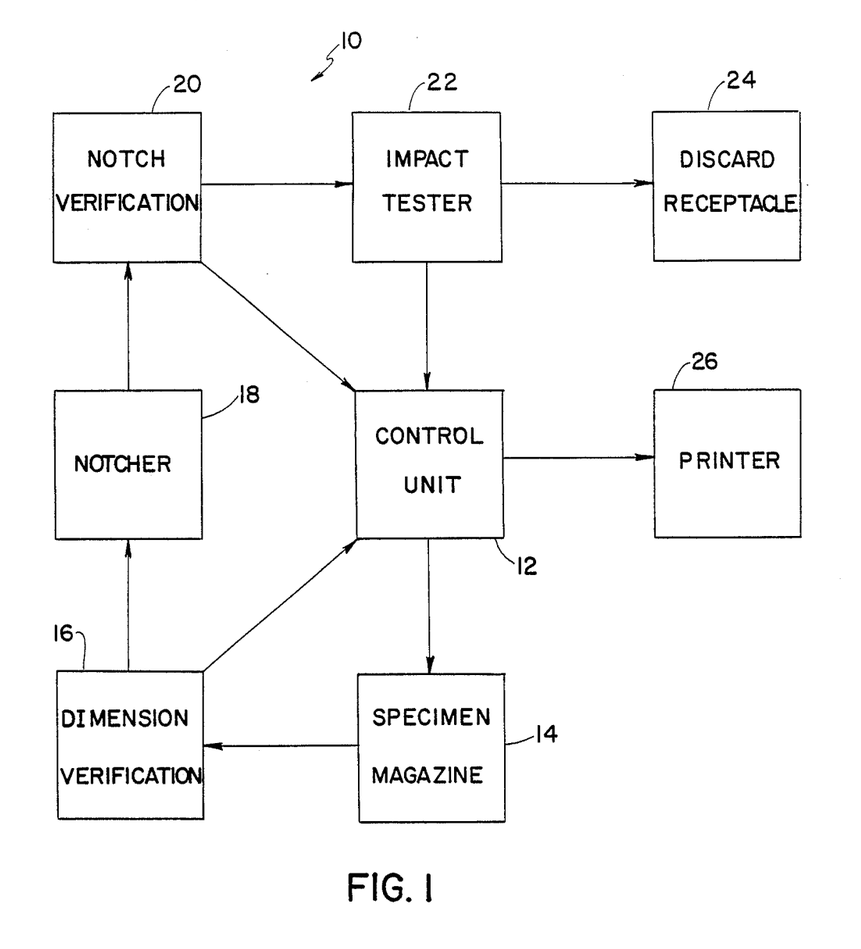
FIG. 1 is a schematic block diagram showing the interrelationship of components and process steps in accordance with the subject invention.

The apparatus 10 further comprises a specimen magazine 14 which is operative to receive, store and sequentially feed a plurality of plastic specimens. Preferably, the specimen magazine 14 is operative to receive and sequentially dispense at least sixty specimens. The specimens may be manually fed into a magazine permanently attached to the apparatus. Alternatively, the magazine may be operative to receive a cassette that had been preloaded with a plurality of specimens at a different location. In still further embodiments, the magazine 14 may be removably mounted to a feed mechanism of the apparatus 10.

Specimens fed from the magazine 14 are sequentially fed to a dimension verification station 16. In particular, the dimensional verification station 16 comprises a transducer which is operative to assess at least the thickness of each specimen to an accuracy of ±0.001 inch. The exact measured dimension is reported to the control unit 12 and becomes an input variable for assessment of the impact strength of the plastic.

Specimens are automatically and sequentially advanced from the dimension verification station 16 to the notcher 18. The notcher 18 is operative to securely retain a linear array of specimens such that the broad rectangular surfaces thereof are in face-to-face contact. The notcher 18 includes a cutting wheel having a V-shaped cutting edge corresponding to the specified shape of the notch required in the specimens. The notcher is operative to complete the notching on a plurality of the specimens, such as a complete test group.

A notch verifier 20 is operatively connected to the notcher and comprises electromechanical or electro-optical means for assessing the accuracy of the notch in each specimen. In particular, the precision of the notch substantially affects the impact test results in that the notch determines the depth of the plastic material being broken by the impact tester. As noted above, the depth of the notch is required by ASTM specifications to be such that the material below the notch is in the range of 0.400±0.002 inch. Specimens having a notch depth outside the specified range will be tested, but the deviation will be noted.

The apparatus 10 further comprises an impact tester 22. As will be explained and illustrated in greater detail below, the impact tester 22 comprises a means for sequentially delivering specimens to a vise such that the notch therein is aligned with the top of the vise as specified by ASTM standards. The vise is then tightened to securely retain the specimen, and the impact hammer is dropped through its arc to strike the specimen. The impact tester 22 further comprises photoelectric means for assessing the type of break. Information pertaining to both the impact and the type of break are reported to the control unit and recorded for each specimen tested. The impact tester 22 further comprises a robotic means for removing the remains of the tested specimen and depositing these remains in a receptacle 24.

The testing is carried out continuously and automatically until all of the specimens loaded into the magazine 14 have been tested. The results may be displayed by a printer 26 either continuously at the end of each specimen testing, periodically at the end of each test group or at the termination of the entire test run. Typically, the printer 26 will provide a separate printed report for each test group.

Figure 2:
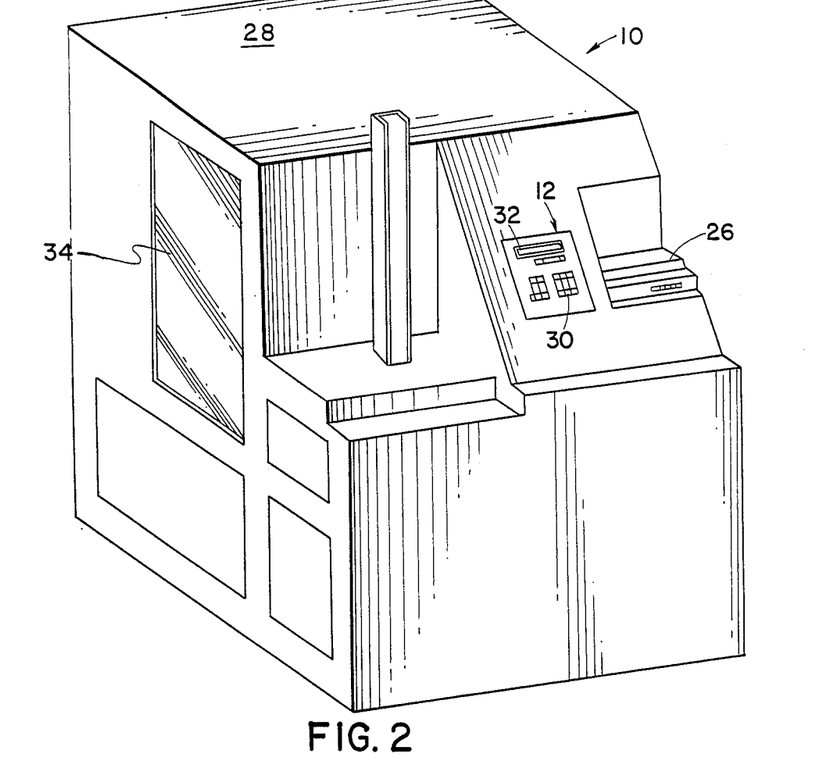
FIG. 2 is a perspective view of the assembled apparatus in accordance with the subject invention.

The apparatus 10 schematically shown in FIG. 1 is illustratively shown in FIGS. 2 and 4–10. The apparatus 10 typically will comprise a housing 28 as shown in FIG. 2 to cover and protect the various operative parts of the apparatus. The magazine 14 extends from the housing 28 to permit the specimens to be readily loaded therein. The control unit 12 includes a key pad 30 for entering pretest data, and a display panel 32 which permits the operator to visually inspect the pretest data being entered prior to actual performance of the test. The printer 26 is depicted as being an integral part of the test apparatus 10. However, it is envisioned that certain embodiments will include the printer at a location from the testing apparatus 10. The apparatus 10 may further be provided with a plurality of windows, such as the window 34 to permit visual inspection of the testing process.

Figure 3:
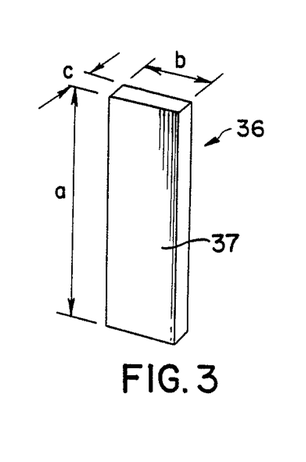
FIG. 3 is a perspective view of a plastic specimen prior to notching.
Figure 4:
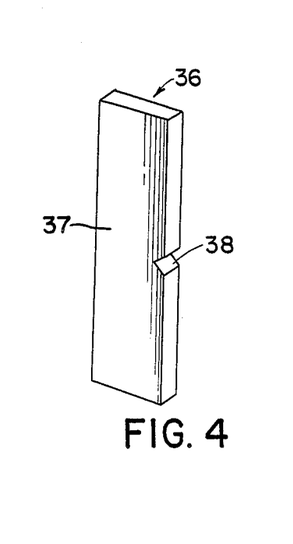
FIG. 4 is a perspective view of the plastic specimen after being notched by the subject apparatus, but prior to testing.

With reference to FIG. 3, the specimens 36 loaded into the magazine 14 are substantially rectangular plastic members having a length "a" of 2.500 inches, a width "b" of approximately 0.500 inch defining major faces 37 and having a thickness "c" which may vary depending upon the test being run. In the typical situation, the width "c" will equal 0.125 inch. As will be explained further herein, each specimen 36 will be machined to create a notch 38 centrally on one longitudinal side thereof and intermediate the opposed longitudinal ends as shown in FIG. 4. The notch 38 is dimensioned to leave a distance "d" of 0.400 inch±0.002 inch below the notch 38.

The entire testing apparatus 10 is shown in greater operative detail in FIGS. 5–10. In particular, the apparatus 10 comprises magazine 14 which is dimensioned to store specimens stacked vertically in a side-to-side linear array. In particular, the magazine 14 is dimensioned to receive an array comprising up to sixty of the specimens 36. However, the apparatus 10 and the magazine 14 are operative with as few as three specimens 36 mounted therein.

Figure 6:
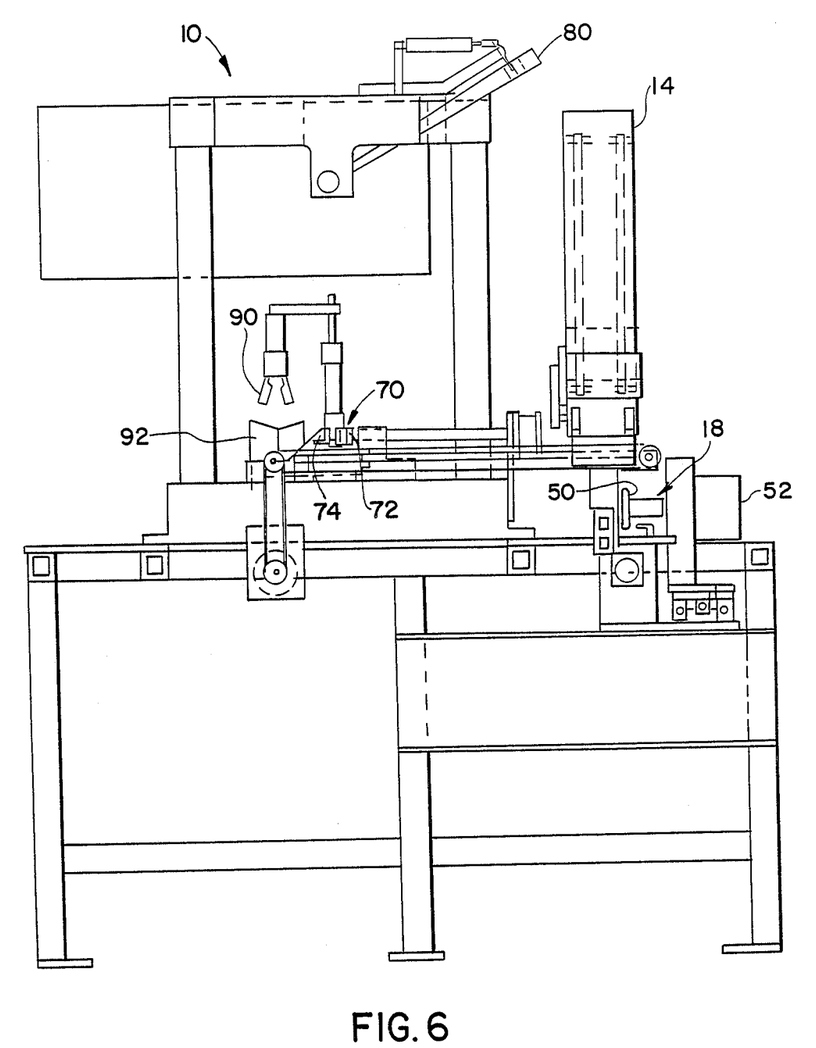
FIG. 6 is a rear elevational view of the apparatus shown in FIG. 5.

The magazine 14 is operative to feed the specimens 36 therefrom to the dimensional verification station 16 which, as shown in FIG. 6, includes a transducer 40. The transducer 40 is operative to precisely measure the thickness of each specimen. The transducer 40 is operatively connected to the control unit such that the measured thickness "c" of each specimen 36 is temporarily stored in the memory of the control unit for use in subsequent analyses of test results.

Figure 7:
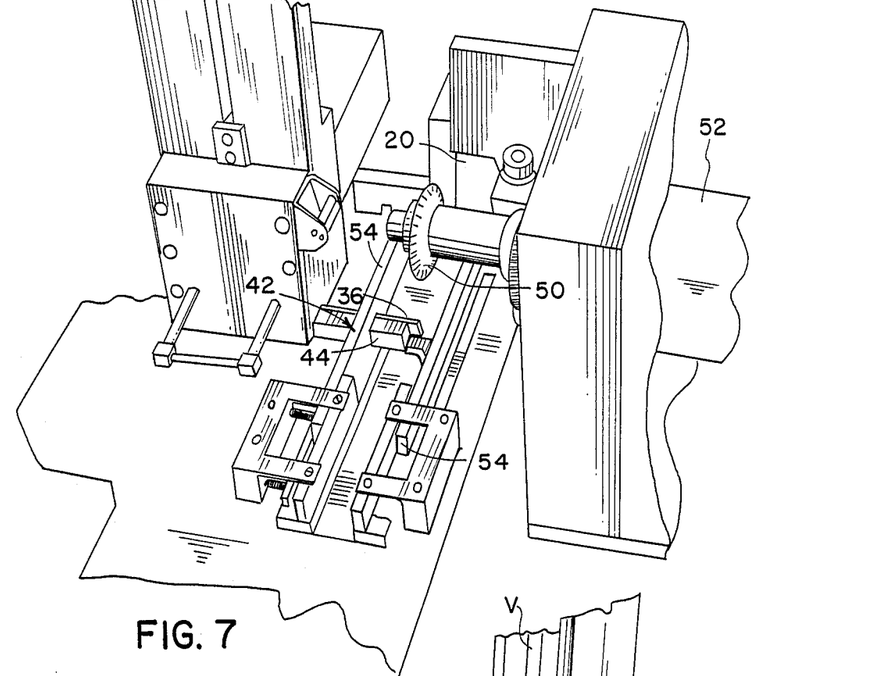
FIG. 7 is a perspective view of the notching apparatus of the subject invention.
Figure 8:
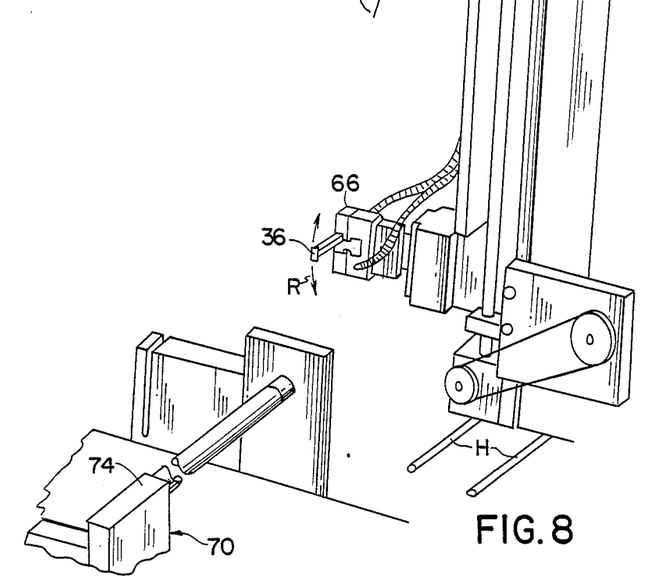
FIG. 8 is a perspective view of the gripping apparatus for moving a specimen to the vise for subsequent impact testing.

The specimens 36 are next fed sequentially to the notcher 18 which is shown most clearly in FIG. 7. In particular, the notcher 18 comprises a clamp apparatus 42 having a specimen pusher clamp 44 which is movable for securely clamping a plurality of specimens 36 with their major front and rear faces 37 in face-to-face abutting relationship. In particular, the clamp apparatus 42 is operative to clamp the array of specimens 36 at least along a front-to-rear axis and a top-to-bottom axis. The notcher 18 further comprises a cutting wheel 50 which is rotatably driven by a motor 52 and which is translatable parallel to the rails 54 to traverse the length of the array of specimens 36. The translation and rotation of the cutting wheel 50 is operative to cut notches 38 centrally in one longitudinal side of each specimen 36 in the clamp apparatus 42. The rotational speed of cutting wheel 50 and the speed of translation along rails 54 are variable and selectively controllable.

The depth of the notch 38 in each specimen 36 is verified by the verification means 20 which comprises a V-shaped anvil having a transducer means operatively connected thereto. The depth of the notch is verified by the amount of movement of the anvil as sensed by the transducer. The notch verification means 20 has settable limit that can be varied for different tests. The notch verification means 20 is operatively connected to the control means to ensure that test results for specimens having an unacceptable notch are clearly identified in the analyses.

Figure 5:
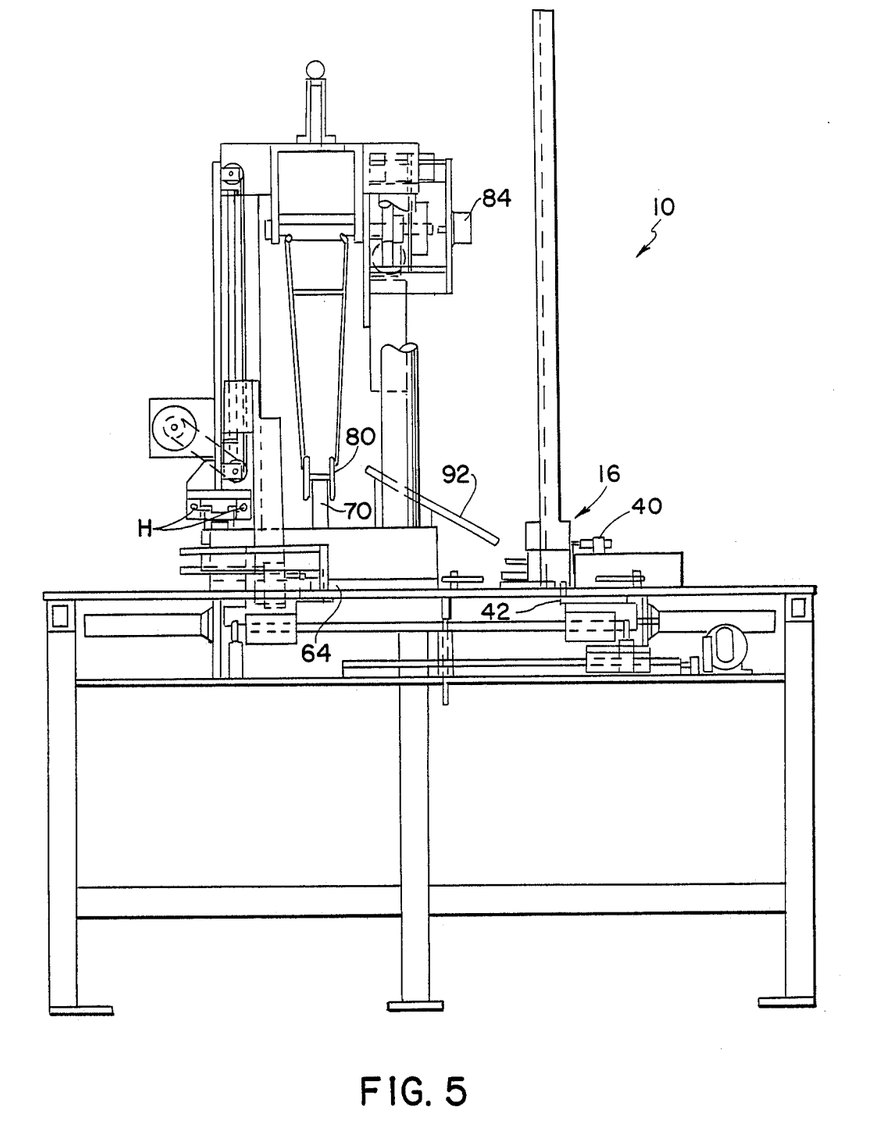
FIG. 5 is a side elevational view of the apparatus minus its outer housing.
Figures 9, 10:
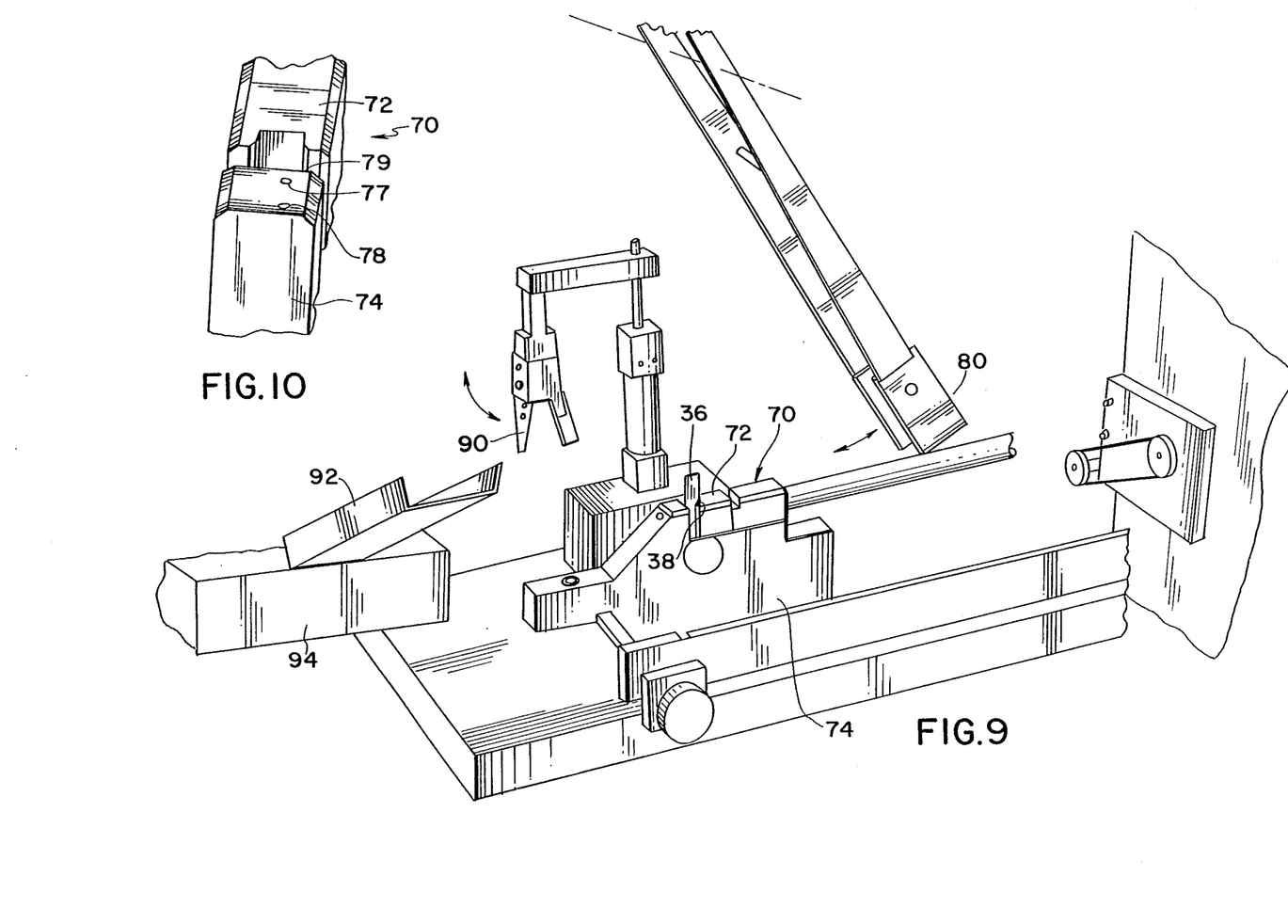
FIG. 9 is a perspective view showing the specimen mounted in the vise.
FIG. 10 is a perspective view of the photodetector.

After the notches 38 in the specimens 36 have been cut and verified, the entire test group is advanced to a test staging area 64 as shown in FIG. 5. In particular, the test staging area 64 comprises an ejector which ejects the specimens 36 sequentially into a position to be received by the gripper 66, as shown most clearly in FIG. 8. The gripper 66 is operative to grab the waiting specimen 36, and to selectively rotate the specimen 36 about a horizontal axis, to move the specimen vertically along rails V or to move the specimen horizontally along rails H. By controlling these movements, the gripper 66 is operative to move the specimen 36 into the vise 70 as depicted in FIG. 9. More particularly, the gripper 66 is operative to ensure that the notch 38 in each specimen 36 is properly aligned with the top of the vise 70. Once the specimen 36 is properly aligned, the vise jaw 72 moves to firmly hold the specimen 36 against the vise base 74. The gripper 66 then releases the specimen 36 and returns to the vicinity of the staging area 64 to grip the next specimen 36 ejected therefrom.

Once the specimen 36 has been securely gripped in the vise 70, the test is ready to commence. In particular, the hammer 80 is released from its locked position above the vise 70 and is permitted to pendulously swing into contact with the specimen 36. The impact of the hammer 80 on the specimen 36 is measured, and the reading is reported to the control unit. The hammer 80 comprises a brake to catch the hammer 80 after the impact.

The base 74 of the vise 70 is provided with a plurality of optical sensors 77, 78 which are disposed at different respective distances from the clamping face 79 of the base 74. In particular, the optical sensors 77, 78 are operative to sense the presence of an object directly in the path of the beam emitted by the optical sensors 77, 78. Thus, the optical sensors 77, 78 will be operative to sense the presence of the top half of a specimen 36 that is broken by the hammer 80 during the test. By comparing the signals sensed by the optical sensors 77, 78, the specific type of break can be assessed. In particular, a failure of either sensor 77 or 78 to sense the presence of the top half of a specimen 36 indicates that a complete break occurred during the test. A signal sensed by the optical sensor 77 closest to the clamping face 79 of the base 74 without a corresponding signal sensed by the optical sensor 78 is indicative of a partial break in the specimen 36. A signal sensed by both optical detectors 77 and 78 is indicative of a more complete hinged break. The photodetectors 77, 78 are operatively connected to the control unit such that the data pertaining to the break type is reported to the control unit and is at least temporarily stored therein for inclusion in the test report.

Upon completion of the test, the hammer 80 is returned pneumatically to its starting position by motor 82 which is shown in FIG. 5, and is retained in that position until the next specimen 36 is properly in position in vise 70 to be tested.

The apparatus 10 further comprises specimen removal grippers 90, as shown in FIG. 6, which are operative to grip the remains of the specimen 36 securely retained in the vise 70 after completion of the test. Upon secure gripping of the remains of the specimen 36, the vise jaw 72 is slidably moved away from the base 74 and the specimen removal grippers 90 move the remains of the specimen 36 to the discard chute 92. The grippers 90 then release the remains of the specimen 36, thereby permitting the specimen 36 to gravitationally fall along the chute and into an appropriate receptacle 94. At this point in the process, the vise 70 is in an open position and ready to accept the next specimen 36. Simultaneously, the next specimen 36 is ejected from the staging area 64 and into the awaiting gripper 62 for transportation to the open vise 70, as explained above.

Upon completion of each test run, the data stored by the control unit is analyzed, and a report is prepared on the printer 26.

In summary, an apparatus and continuous process for testing plastic specimens is provided. The apparatus comprises means for sequentially feeding each of a plurality of plastic specimens, means for dimensionally verifying the thickness of each specimen, a notcher for cutting a notch of the required depth in each specimen, a notch verification means for checking the accuracy of the notches and an impact tester. The impact tester comprises a first gripper which is operative to move the specimen sequentially into a vise and an impact hammer which is automatically activated to pendulously swing into the specimen. The impact test portion of the apparatus comprises means for assessing the impact and photodetector means for assessing the type of break caused by the impact. The impact tester further comprises a second gripper for removing the remains of the specimen from the vise and depositing the remains in an appropriate receptacle. A control unit receives and analyzes input data from both the operator and from the various components of the apparatus. The control unit is in communication with a printer which is operative to print a test report for each test group of specimens, based upon the analyses performed by the control unit.

While the invention has been described with respect to a preferred embodiment, it is apparent that various changes can be made without departing from the scope of the invention as defined by the appended claims.

What is claimed is:

1. An impact tester for the impact testing of each of a plurality of specimens, said tester comprising:
    vise means for selectively gripping one said specimen;
    delivery means for sequentially delivering specimens to said vise means;
    hammer means for selectively subjecting one said specimen gripped in said vise means to a selected impact and for measuring the impact of said hammer on the specimen;
    photodetector means in proximity to said vise means for detecting and identifying a break in said specimen in response to the impact of said hammer means; and
    control means operatively connected to said hammer means and said photodetector means for displaying information relating to the impact of said hammer means on said specimen and the type of break identified by said photodetector means.

2. An impact tester as in claim 1 further comprising measurement means for measuring at least a portion of each said specimen prior to subjecting each said specimen to the impact of said hammer means, said measurement means being operatively connected to said control means.

3. An impact tester as in claim 2 further comprising notching means for forming a notch of a predetermined depth at a selected location in each said specimen, said notching means being disposed at a location to create said notch prior to the delivery of said specimen to said vise means.

4. An impact tester as in claim 3 further comprising notch verification means for measuring the dimensions of said notch formed by said notching means, said notch verification means being operatively connected to said control means for identifying specimens having a notch dimension outside a specified range.

5. An impact tester as in claim 4 further comprising a magazine means for storing a plurality of said specimens and for delivering said specimens sequentially to said measurement means.

6. An impact tester as in claim 1 wherein said hammer is pendulously mounted to said impact tester for swinging from a start position into contact with one said specimen mounted in said vise means, and wherein said hammer means further comprises return means for returning the hammer to the start position after the hammer has been impacted thereby.

7. An impact tester as in claim 1 further comprising disposal means for disposing of at least portions of each said specimen secured in said vise means after the subjection of the specimen to the impact by said hammer means.

8. An impact tester as in claim 1 further comprising a printer operatively connected to said control means for printing selected results of said impact test.

9. An impact tester as in claim 1 wherein said photodetector means comprises a plurality of photodetectors securely mounted adjacent said vise means at a location thereon generally in alignment with the specimen mounted therein and on the side of the specimen opposite the side thereof impacted by the hammer, said photodetectors being at different respected distances from the specimen mounted in the vise means.

10. A process for subjecting each of a plurality of specimens to impacts sequentially imparted to said specimens, said process comprising the steps of:
    providing a supply of specimens;
    sequentially securing each said specimen at a predetermined location;
    subjecting each said secured specimen to a predetermined impact;
    measuring the response of said specimen to said impact; and
    photoelectrically identifying the existence and type of break in said specimen by said impact.

11. A process as in claim 10 further comprising the step of cutting a notch in said specimen at a predetermined location thereon.

12. A process as in claim 11 further comprising the step of verifying the dimensions of the notch cut in each said specimen.

13. A process as in claim 12 wherein the step of providing a plurality of specimens comprises the step of placing a plurality of said specimens in a magazine, and wherein said process further comprises the steps of sequentially feeding said specimens from said magazine and measuring at least one dimension of each said specimen fed from said magazine.

14. A process as in claim 11 wherein the step of securing each said specimen at a predetermined location comprises the step of aligning said notch at a predetermined position in a vise.

15. A process as in claim 11 wherein the step of cutting a notch in said specimen comprises the steps of securely gripping a plurality of said specimens in a generally linear array and cutting notches in the specimens in said array.

16. A process as in claim 10 further comprising the step of discarding at least portions of each said specimen after completion of each said test.

17. A process as in claim 10 further comprising the step of preparing a written test report for at least one of said specimens subjected to said test.

* * * * *